United States Patent [19]

Perkins

[11] 4,150,287
[45] Apr. 17, 1979

[54] OPTICAL SYSTEM FOR USE WITH COLOR SORTER OR GRADER

[75] Inventor: Joseph R. Perkins, Burke, Va.

[73] Assignee: AMF Incorporated, White Plains, N.Y.

[21] Appl. No.: 874,169

[22] Filed: Feb. 1, 1978

[51] Int. Cl.² ............................................... G01J 3/50
[52] U.S. Cl. ..................................... 250/226; 250/227
[58] Field of Search ................ 250/226, 227; 209/580, 209/581

[56] References Cited

U.S. PATENT DOCUMENTS 3,981,590 9/1976 Perkins ............................ 250/226 X

*Primary Examiner*—David C. Nelms
*Assistant Examiner*—Darwin R. Hostetter
*Attorney, Agent, or Firm*—George W. Price; John H. Gallagher

[57] ABSTRACT

An optical system for use with apparatus for grading articles of produce according to color. The simplified system is comprised of an aspherical lens, a field stop and an end of a fiber optic bundle at the image plane of the lens. Color filters and photoelectric detectors are positioned from the opposite end of the bundle at a distance so as to be uniformly illuminated by light emanating from each fiber of the bundle upon which a portion of the image is present.

15 Claims, 4 Drawing Figures

OPTICAL SYSTEM FOR USE WITH COLOR SORTER OR GRADER

BACKGROUND OF THE INVENTION

In my U.S. Pat. No. 3,981,590 I disclose an optical system for use in grading and/or sorting agricultural produce such as tomatoes, apples, and tobacco leaves, according to their colors. My present invention is an improvement over that prior system because it is simpler, less expensive, and more effective to illuminate electo-optic detecting means that are responsive to the monitored color components in the light received from articles being graded.

As I discussed in my earlier patent, the automatic grading of agricultural produce such as tomatoes and apples for example, the articles of produce are moved in alignment along a conveyor and past an inspection position where they are automatically graded and then sorted according to some desired characteristic of the produce. Quite commonly, the basis for grading is the color of the articles and the grading decision is based on the comparison of two or more electrical signals which are functions of respective color components of light that is reflected from the articles onto photoelectric detectors. This general method of grading agricultural products is well known and need not be further described.

In sorting articles of produce according to color, the grading classification will include a given range of color and intensity variations. The optical system associated with the photodetectors of the color grader must be good enough that the variation in color and intensity of light reflected from a single article and transmitted through the optical system is well within the range of variations established for grading the particular produce.

In a moving conveyor type of produce grader the high speed of movement of the articles through the field of view of the detectors, the variation in sizes of the articles, the vibration and sometimes rolling of the articles on the conveyor all cause the viewing distance and viewing angle to vary as the articles pass through the field of view. With an inadequate optical system these variable factors can cause significant variations in the color and intensity of light transmitted by the optical system and received by the color detectors. The result has been that the detectors have produced inconsistent signals, thus causing the electronic grading equipment to compare color signals which were not truly representative of the color components of the article being viewed at a given instant of time.

One type of optical system used in the past to direct reflected light onto a plurality of spaced color detectors was comprised of an objective lens, a field stop, and a field lens, wherein the field lens was intended to present equally to two or three spaced apart color detectors the light from the field of view which enters the objective lens from objects in the field of view. That is, the field lens focused the image of the clear aperture of the objective lens onto the detectors. However, if the article being viewed were not exactly in focus at the field stop during any part of its travel through the field of view, the possibility existed that not all the detectors would be equally illuminated. Additionally, as the object moved across the field of view of the lens system, the angle of the light reflected back to the optic system constantly changed so that it was possible that all the detectors did not receive the same amount of light even if the object were in focus. The nonuniform illumination of the detectors gave rise to the generation of erroneous color component signals and resulted in erroneous grading.

In my U.S. Pat. No. 3,981,590 I disclose an optical system that included an objective lens, a field stop, a field lens, a fiber optic bundle, a light diffuser and a light guide for substantially equally illuminating color filters that are at equal distances from the optic axis and in front of respective photodetectors. That improved system has been used successfully for color grading different types of agricultural products.

My optical system of this invention is a further improvement and is comprised of a short focal length lens, a field stop of the appropriate size and shape to provide the required field of view, a fiber optic bundle positioned against the back side of the field stop, and a filter-detector assembly that is substantially uniformly illuminated by the received light that passes through the fiber optic bundle. A plurality of detector means in the assembly produce respective electrical output signals that are functions of respective color components in the received light. Appropriate mounting, spacing, and housing means including a tubular barrel maintain the above-mentioned components in their required relative positions. My improved system does not require the field lens, the light guide, or the diffuser of my earlier system and thus is simpler, less expensive, and is easier to manufacture, operate and maintain. Although it is practical to do so, it is not a requirement of my present system that all filters be positioned the same distance from the optic axis of the system. The filters may be located anywhere within a region that is uniformly illuminated by any portion of the object in the field of view.

The invention will be described by referring to the accompanying drawings wherein.

DETAILED DESCRIPTION OF PREFERRED EMBODIMENT

Figure 1:
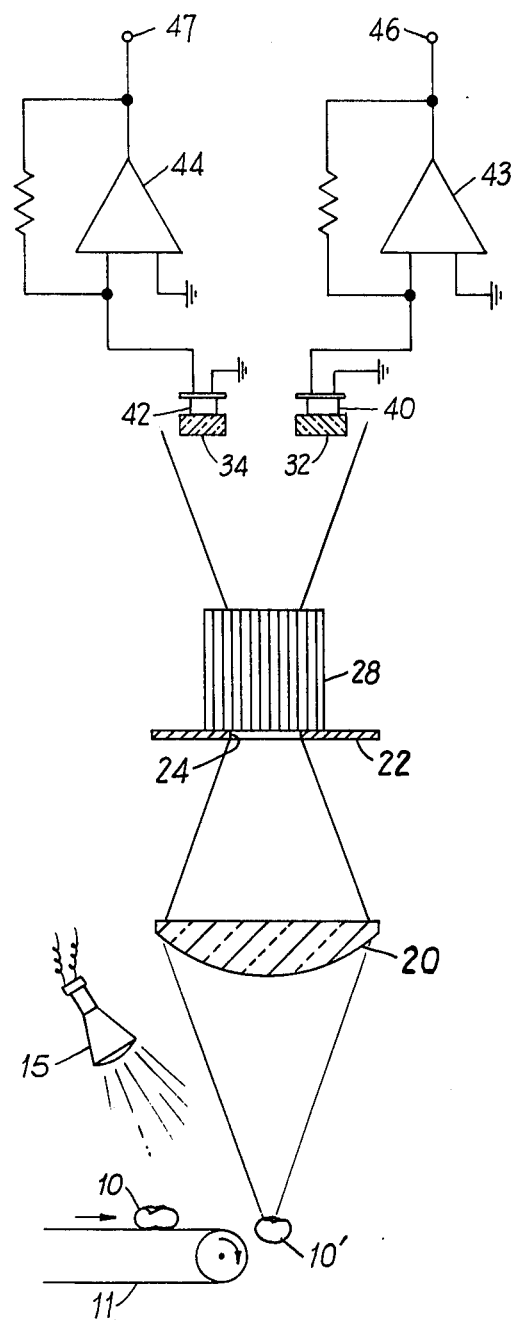
FIG. 1 is a simplified sketch illustrating an embodiment of my invention.

FIG. 1 is a simplified illustration of the present invention as used in a color sorter for sorting tomatoes. This is but one example of the possible uses for the present invention. Tomatoes 10 to be sorted are carried on a conveyor 11 and are discharged from the end of the conveyor along a free fall path. As the tomatoes leave the end of conveyor 11 they successively pass through an inspection position where they are illuminated by a polychromatic light source 15. Light reflected from a tomato 10' at the inspection position is directed to and substantially uniformly illuminates objective lens 20. An image of the tomato is focused in the plane of a field stop 22 that has an aperture 24. Immediately behind and in contact with the back surface of field stop 22 is a jacketed fiber optic bundle 28. Fiber optic bundle 28 is comprised of a multitude of optical fibers or optical glass light pipes that are gathered into a tight bundle to form an integral unit. The functioning of fiber optic bundle 28 will be described in more detail below.

Light emanating from fiber optic bundle 28 is in a diverging pattern and is incident on the plurality of different color filters 32, 34. The color components of light that pass filters 32 and 34 are incident on respective photodetector devices 40 and 42. The color components incident on detectors 40, 42 may be red and green, for example. Only two color filters and two photodetectors are illustrated in FIG. 1 for simplicity purposes. Three, four, or more color filters and a like number of photodetectors may be used if desired. The number of filters and detectors used is not part of the present invention. However, by following the teachings of this invention, the area occupied by the color filters will be substantially evenly illuminated by incident light from any portion of the tomato that falls within the field of view.

Photodetectors 40, 42 produce electrical output signals that are functions of the intensities of the respective color components that are incident on them. The respective signals are amplified in amplifiers 43 and 44 and are coupled to output terminals 46 and 47. These terminals may be connected to the input terminals of electronic grading and/or sorting equipment that operates on the signals to provide an indication of given characteristics of the article being inspected. A number of grading and sorting systems are known. As an example, suitable tomato sorting equipment is marketed under the trademark Perceptor by AMF Incorporated, Herndon, Virginia. The three color grading system described in U.S. patent application Ser. No. 765,716 in the name of J. R. Sherwood is an example of such equipment.

Figure 2:
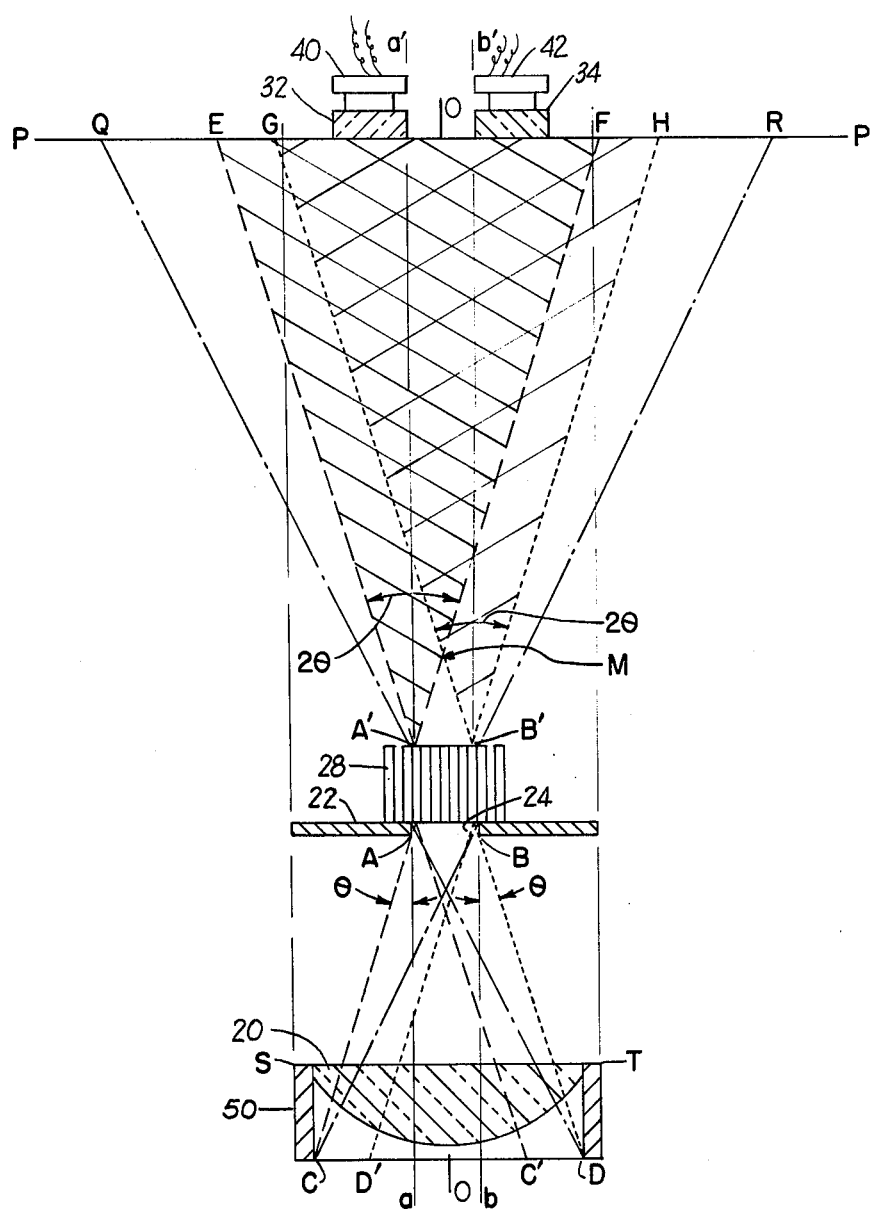
FIG. 2 is a simplified diagram used in the explanation of the operation of my invention.

The functioning of the optical system will be explained in more detail by referring to FIG. 2. Objective lens 20 is shown positioned within a cylindrical shield 50. Lens 20 is an aspheric lens having as low an "f-number" as can be used without unreasonable complications and expense. As an example, I have used a lens with a focal length of 34.5 mm and a diameter of 38 mm. Field stop 22 is positioned in front of the left end of optic fiber bundle 28, this end surface being the image plane of the object. The dimensions of the aperture 24 are much smaller than the diameter of objective lens 20 for reasons to be discussed below. The opposite edges A and B of the aperture represent the extreme points of the aperture that are furtherest from the optic axis O—O of the optic system. For example, aperture 24 is an elongated rectangular slot and the optic axis passes through its center. Points A and B are at diagonally opposite corners of the slot.

Fiber optic bundle 28 is in contact with the back side of field stop 22. The fibers extend generally parallel to the optic axis and may be either randomly or nonrandomly oriented in the bundle. In analyzing the system of FIG. 2, it will be assumed that ray paths CA and DB define the light paths from the opposite edges of the lens clear aperture through opposite edges of field stop 22. Conditions and parameters are chosen so that lens 20 is substantially uniformly illuminated by at least a portion of an object in the predetermined field of view and that all of aperture 24 in field stop 22 is illuminated by the clear aperture of lens 20. Clear aperture is defined as the area of the lens through which light passes without interference from the lens mounting.

Light incident on the left end of fiber optic bundle 28 is guided through the bundle by individual optic fibers and emerges from the right side of the bundle. The acceptance angle through which the fiber optic bundle accepts slight must be large enough to receive light uniformly from all parts of the lens. This typically means that the numerical aperture of the fiber optic i.e., $\sin \theta$, must be greater than 0.5, a requirement that is easily met.

Figure 3:
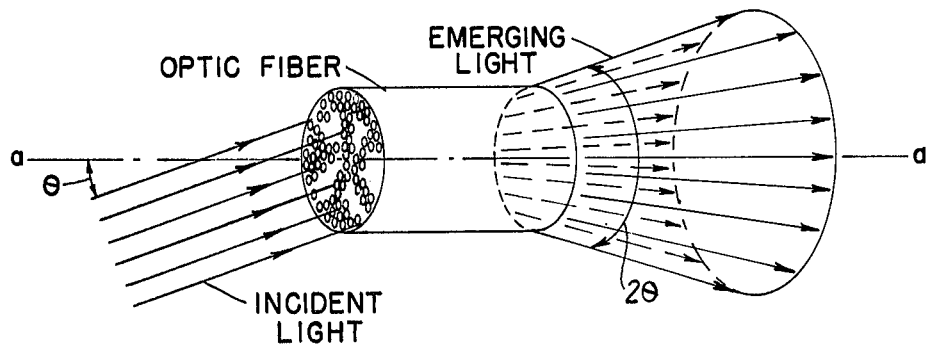
FIG. 3 is a simplified diagram illustrating the functioning of an optical fiber.

The operating characteristic of an optic fiber is illustrated in the simplified sketch of FIG. 3 which illustrates that a beam of light that is incident on the end of an optic fiber at an angle $\theta$ to the fiber axis a—a emerges at the far end in a light cone whose apex angle is $2\theta$.

Referring again to FIG. 2, and keeping in mind that point A is where a point at one limit of the field of view is focused, ray CA is incident on the left face of fiber optic bundle 28 at an angle $\theta$ to the axis a–a' that passes through point A parallel to optic axis o–o'. The ray passes through a fiber in the bundle 28 and emerges on the surface of the cone of light EA'F that is illustrated with dashed and slanting lines. All light passing through point A at the angle $\theta$ is on the surface of a cone defined by CAC'. This input hollow cone of light emerges from fiber optic bundle 28 on the surface of cone EA'F. Furthermore, because of the functioning of optic fibers, light within the solid right circular cone CAC' passing through point A and incident on fiber optic bundle 28 is the source of light for the solid right circular light cone EA'F on the output side of bundle 28. The light within the circle whose diameter is EF on plane PP is of uniform intensity since its source is the associated uniformly or evenly illuminated circle CC' in the lens clear aperture. Note that the circle of light CC' is the largest circle in the lens clear aperture that can be drawn about the axis a–a'. Hence, circle EF in plane PP is the largest circle for which light from point A is uniform or even. Radially beyond the circle EF in plane PP the intensity of light from point A falls off until the circle having radius a'Q is reached. Light at point Q corresponds to light in ray path DA. Beyond the radius a'Q there is no illumination from point A.

In a similar analysis, another ray DB emanating from an opposite point in the field of view passes through point B at the opposite edge of aperture 24 and is incident on the left face of fiber optic bundle 28 at the angle $\theta$. This ray emerges on the surface of a cone GB'H whose apex angle is $2\theta$, as illustrated by the dotted and oppositely inclined hatched lines. Again due to the functioning of optical fibers, all light in the right circular solid light cone DBD' passing through point B and incident on the fiber optic bundle 28 is the source of light in the right circular solid light cone GB'H. Light within the circle whose diameter is GH on plane PP is of uniform intensity since its source is the uniformly or evenly illuminated circle DD' in the lens clear aperture.

The two light cones EA'F (dashed lines) and GB'H (dotted lines) are coincident throughout the region illustrated by the double cross hatched region GMF. The coincident region on plane PP defined by the limits GF was established by light passing through the opposite extreme limits A and B of the field stop aperture 24. Consequently, light from each small area in the focused image in aperture 24 between the limits A and B will pass through fiber optic bundle 28 and will emerge in a corresponding cone that uniformly or evenly illuminates the plane PP in a respective circle that includes the area having the limits GF. Therefore, if color filters 32, 34 and photodetectors 40 and 42 of FIG. 1 are positioned in plane PP in the coincident region whose illustrated limits are GF, every small area of the skin of a tomato in the field of view will evenly illuminate all the color filters. In other words, all detectors are within the cone of light emanating from each fiber of the fiber optic bundle on which the image of the object is focused. (It is to be understood that all of the small areas of the tomato that are in the field of view may not produce the same illumination, and that the cones of light from all of the individual fibers are not necessarily of the same intensity).

Because of the above described characteristics of the optical system of this invention, each of the filter-detector pairs of the system is looking at the same part of the object. This is true even though the object may be somewhat out of focus. Without the use of the fiber optic bundle each filter-detector pair would be looking at a different part of the object when the object is out of focus, which is an undesirable situation.

The circle of uniform illumination produced on plane PP by each optic fiber results from a respective uniformly illuminated circle on the lens clear aperture. As a result, a dirt spot on the lens will not render any given filter-detector pair ineffective.

In practice it is undesirable to have light "bouncing around" within the optical system. Consequently, means are provided for attenuating to the maximum extent possible, all light that crosses the horizontal lines SG and TF in FIG. 2. These light attenuating means will be discussed in connection with the description of FIG. 4.

Figure 4:
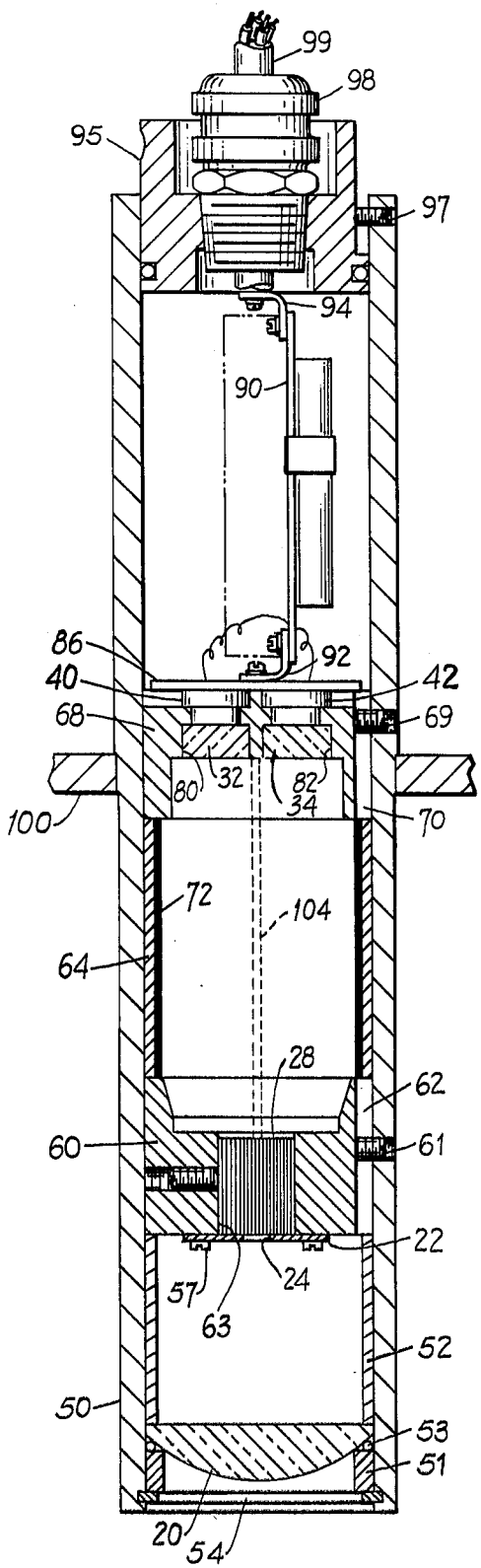
FIG. 4 is an illustration of optical apparatus constructed in accordance with my invention.

A practical embodiment of my improved optical system is illustrated in FIG. 4. The entire assembly is housed within an optical barrel 50 comprised of an aluminum tube, for example. Aspheric lens 20 is positioned within the end of barrel 50 so that the end of the barrel serves as a shield. Optical spacer tubes 51, 52 and elastomeric O-ring 53 support lens 20 within barrel 50. A retaining ring 54 secured with a circular slot in barrel 50 maintains lens 20 and its adjacent parts in fixed position within the barrel.

Field stop 22 is a thin disc that has a narrow rectangular slot 24 centrally and symmetrically located relative to optic axis O—O. The disc is attached by screws 57 to a cylindrical mounting insert 60. Insert 60 is fixed in position by set screw 61 that passes through an alignment slot 62.

An axially extending cylindrical aperture or bore 63 extends from the left face of mounting insert 60 and provides a receptacle for securely holding jacketed fiber optic bundle 28 against the back side of field stop 22. Bundle 28 is in registration with aperture 24 in field stop 22 to receive light that passes through the field stop. An additional set screw that is threadably engaged in mounting insert 60 holds the jacketed fiber optic bundle in place.

An optical spacer tube 64 is located to the right of mounting insert 60 and butts against the end of filter-detector assembly mounting insert 68. Set screw 69 passes through barrel 50 and alignment slot 70 to hold the insert in position. The inside surface of optical spacer tube 64 is provided with a light attenuating surface 72 that prevents diverging light from being reflected onto the filter-detector assembly. In practice I used a light absorbing black material called flock paper, obtainable from Edmund Scientific Company, Barrington, New Jersey. This paper has an adhesive side that may be secured to the inside of optical spacer 64. Baffles or any other type of light attenuating means may be used to eliminate the diverging light.

Filter-detector assembly insert 68 includes a plurlity of recesses 80, 82 symmetrically disposed around the optic axis O—O. Color filters 32 and 34 are received within the recesses. Disposed within the right end to insert 68 and immediately behind filters 32 and 34 are photodetectors 40 and 42 for receiving respective color components of light that pass through the filters. Photodetectors 40, 42 are mounted on a printed circuit card 86 that butts against the end of mounting insert 68.

The electrical leads from photodetectors 40 and 42 are connected to a printed circuit board 90 that includes preamplifiers for the respective photodetector outputs. Circuit board 90 is mounted by brackets 92 and 94 between printed circuit card 86 and an end plug 95. Set screw 97 maintains plug 95 in position at the end of barrel 50. Feed-through 98 is threaded into end plug 95 and supports cable 99 whose conductors carry the color component signals that are coupled to electronic grading apparatus.

A mounting bracket 100 is secured to barrel 50 for mounting the entire assembly on grading apparatus.

An optical system constructed in accordance with the teaching of this invention for grading tomatoes according to their colors employed the following components and had the following approximate dimensions.

Optic barrel 50 — 8.62 inches long: 1.875 inches O.D.: 1.499 inches I.D. — Black anodized aluminum.

Lens 20 — 37.5mm diameter: 12mm thick on axis: 34.5mm focal length, Part No. 01-LAG-012, Melles Griot Company, Costa Mesa, California.

Fiber Optic Bundle 28 — 0.280 inch diameter × 0.62 inch long: Individual fiber diameter 0.02 inch: Minimum packing fraction = 0.65. Both ends ground and polished Stainless steel jacket 0.312 inch diameter. Product of Welch Allyn Co., Skaneateles Fall, New York.

Field stop 22 — 1.00 inch diameter disc × 0.020 inch thick.

Aperture 24 — 0.093 inch × 0.280 inch slot with rounded ends.

Field of view — 1.4 inch × 0.5 inch.

Optic spacer 51 — 0.250 inch long × 1.490 inches diameter.

Optic spacer 52 — 1.225 inches long × 1.490 inches diameter.

Optic spacer 64 — 1.680 inches long × 1.490 inches diameter.

Spacing from end of optic fiber bundle 28 to photodetectors 40, 42 — 2.715 inches.

Spacing from object to lens 20 — 9 inches.

Light sources — 15 watt sealed beam Tungsol lamps (T3613).

Filters — Four: centered at wavelengths 660, 670, 800, 990nm.

In an optical system constructed according to the present invention and intended to be used in the grading of tobacco leaves, the fiber optic bundle 28 was a commercially available device known as a plano/plano-round face-plate, part number G025P14-06, a product of Galileo Electro-Optics Corp., Sturbridge, Massachusetts. The bundle had an outside diameter of 25mm and was 4mm thick. (Mounting insert 60 will be appropriately shaped to receive this bundle.) Individual fibers have a nominal diameter of 6 microns. The lens was the same as described above. The distance from the back surface of the lens to the front surface of the fiber optic bundle was approximately 1.181 inches and the distance from the back surface of the bundle to the photoelectric detectors was approximately 3.305 inches. The aperture in the field stop had the dimensions 0.126 inch × 0.425 inch. The field of view was 5 inches × 1.5 inches.

In order for the fiber optic bundles to function as described above, the ratio of the length to the diameter of individual fibers desirably should be 10 or greater. It is desirable that the fiber optic bundle not pass any light that does not propagate through the fibers. Bundles having this characteristic are commercially available. It is to be noted that when the fiber optic bundle is placed against the back side of the field stop, the stop is effectively extended along the axis. Consequently, the positioning of the filter-detector assembly is a function of the thickness of the fiber optic bundle.

It also should be understood that a separate field stop may not be required. In such event the jacketed fiber optic bundle provides the function of a separate field stop.

The optical system described above is a simple and effective system. The design and adjustment of this system for optimum effectiveness is considerably less critical than is the system described in my above mentioned patent. In this regard, the positions of field stop means 22 and the front end of fiber optic bundle 28 are not critical. They may be positioned at or near the image plane.

The physical length of optical barrel 50 is shorter than in my prior system by virtue of the fact that I use as short a focal length lens as practical. As indicated in the above data, the ratio of the diameter of the lens to its focal length is a value equal to approximately one. Additionally, the ratio of the diameter of the lens to the major dimension of the field stop aperture should be at least two, and preferably is greater. In the data given above that ratio was considerably greater than two. The above ratios are not critical but are approximation within design ranges.

My present optical system uses fewer component parts than the system described in my prior patent. In that prior system, a field lens was used to focus an image of the objective lens onto the end of the fiber optic bundle. I had to use a diffuser plate in my prior system. In the system of this invention, the objective lens directly focuses an image of the object onto the end of the fiber optic bundle. This system cannot use a diffuser plate without introducing deleterious effects.

In the grading of some produce such as apples it sometimes is desirable to determine what percentage of the surface of the apple is red, for example. In this situation it is desirable that the optical system be able to independently "look" at both halves of a rotating apple so that a red to green color comparison of the two halves may be made by color grading apparatus. Accordingly, there must be two pairs of red and green color detectors, one for each half of the apple. Referring to FIG. 4, filter-detector assembly insert 68 will be provided with four recesses similar to the illustrated recesses 80, 82. The four recesses will be symmetrically distributed about the optic axis and at equal radii from the axis. A septum or divider plate 104 is positioned between the back face of fiber optic bundle 28 and filter-detector assembly insert 68. The divider plate is T-shaped with the cross portion lying along a diameter of insert 68 and extending completely across barrel 50 so that a pair of red and green filters and detectors is on each side of the divider plate 104. The surfaces of divider desirably are coated or covered with nonreflective material.

The divider effectively divides the field of view into two halves so that the pair of red and green detectors on each side of the divider is looking at one half of the object in the field of view.

In practice, the radiant energy illuminating the articles to be graded may be visible light, ultraviolet light, or infrared light. In practical applications using the apparatus described herein, tungsten lamps and fluorescent lamps may be used. In this description and in the accompanying claims, the use of the words light and color is intended to include radiant energy and frequency components thereof within any of the above spectra of light.

In its broader aspects, this invention is not limited to the specific embodiment illustrated and described. Various changes and modifications may be made without departing from the inventive principles herein disclosed.

What is claimed is:

1. An optical system for use with apparatus for grading agricultural produce according to frequency components of radiant energy received from an article of the produce, said system comprising the combination
   objective lens means for focusing at an image plane an image of an article that is within a predetermined field of view,
   field stop means providing an aperture at or near said image plane for defining a field of view that includes an article to be graded,
   a fiber optic bundle comprised of a multitude of light transmitting optical fibers and having first and second ends,
   the first end of the bundle being at or near said image plane on the side thereof opposite said lens,
   a plurality of light filter means positioned relative to each other and at a distance from the second end of the fiber optic bundle to assure that the light from each optic fiber of the bundle that is illuminated by the focused image of the articles produces equal illumination on all filter means, and
   a plurality of photodetector means each arranged to receive light passed by a respective filter means.

2. The combination claimed in claim 1 wherein the light transmitting fibers in the fiber optic bundle each have a ratio of length to diameter of at least 10.

3. The combination claimed in claim 2 wherein the acceptance angle of the fiber optic bundle is great enough for the bundle to receive light substantially evenly from all parts of the lens clear aperture.

4. The combination claimed in claim 3 wherein the fiber optic bundle has a numerical aperture of at least 0.5.

5. The combination claimed in claim 3 wherein the diameter of said objective lens is at least twice the maximum dimension of said field stop aperture.

6. The combination claimed in claim 5 wherein the ratio of the diameter of the lens to its focal length is of the order of approximately one.

7. The combination claimed in claim 6 wherein said lens is an aspheric lens.

8. An optical system for use with apparatus for grading agricultural produce according to frequency components of radiant energy received from an article of the produce, said system comprising the combination
   an elongated hollow barrel,
   an objective lens disposed within said barrel adjacent one end thereof for forming an image of at least a portion of an article of produce at an image plane within said barrel, said lens substantially uniformly illuminated by said article, a field stop within said barrel at or near said image plane of the objective lens to define a field of view that will include at least a portion of an article of produce, a fiber optic bundle within said barrel and comprised of a multitude of fiber optic light guides, said bundle having first and second ends, the first end being positioned at or near said image plane to receive light passing through said field stop, filter-detector means positioned in said barrel in spaced relationship from the second end of the fiber optic bundle, said filter-detector means including a plurality of light filter means spaced relative to each other transversely of the barrel and from the second end of the bundle a distance to assure that all are equally illuminated by light passing through each optic fiber that is illuminated by the focused image, said filter-detector means further including a plurality of photodetector means each positioned to receive light passed by a respective one of the light filter means, means for coupling electrical signals from each of said photodetectors, and means at the end of the barrel opposite the objective lens for passing electrical conductors from the interior to the exterior of the barrel.

9. The combination claimed in claim 8 wherein the individual fiber optic light guides have a ratio of length to diameter of at least 10.

10. The combination claimed in claim 9 wherein the acceptance angle of the fiber optic light bundle is great enough for the bundle to receive light substantially evenly from all parts of the lens clear aperture.

11. The combination claimed in claim 10 wherein said bundle has a numerical aperture of at least 0.5.

12. The combination claimed in claim 10 wherein the diameter of the objective lens is at least twice the maximum dimension of the field stop aperture.

13. The combination claimed in claim 12 wherein the ratio of the diameter of the lens to its focal length is of the order of approximately one.

14. The combination claimed in claim 12 wherein the lens is an aspheric lens.

15. The combination claimed in claim 8 and further including divider means between the second end of the fiber optic bundle and said filter-detector means for dividing into independent portions the light propagating therebetween.

* * * * *